United States Patent [19]

Wood et al.

[11] Patent Number: 5,089,486

[45] Date of Patent: Feb. 18, 1992

[54] BIOCIDAL AZOPHENYL COMPOUNDS

[75] Inventors: William W. Wood; Thomas W. Naisby, both of Sittingbourne; Andrew C. G. Gray, London, all of England

[73] Assignee: Shell Research Limited, England

[21] Appl. No.: 558,462

[22] Filed: Jul. 27, 1990

[30] Foreign Application Priority Data

Aug. 4, 1989 [GB] United Kingdom ............... 8917853

[51] Int. Cl.$^5$ .............. A01N 51/00; A01N 33/26; C07C 291/08; C07C 245/00
[52] U.S. Cl. .............................. 514/149; 514/150; 534/556; 534/557; 534/558; 534/565; 534/566; 534/572; 534/885
[58] Field of Search ............ 534/556, 557, 558, 565, 534/566, 572, 885; 514/149, 150

[56] References Cited

U.S. PATENT DOCUMENTS 3,980,522  9/1976  Umezawa et al. ............ 534/566 X
4,009,155  2/1977  Umezawa et al. ............ 534/556
4,558,040  10/1985  Pilgram et al. .............. 514/150

FOREIGN PATENT DOCUMENTS 52-71444  6/1977  Japan ................... 514/149

OTHER PUBLICATIONS

Calvino et al., *Chemical Abstracts*, vol. 106, No. 84095c, (1987).
March, "Advanced Organic Chemistry", 3rd Ed., John Wiley and Sons, New York (1985), pp. 371–372.
Saunders, "The Aromatic Diazo-Compounds and Their Technical Applications", Edward Arnold and Co. (1949), pp. 142–147.
Gascor et al., *Chemical Abstracts*, vol. 82, No. 125024k, (1975).

Primary Examiner—Mary C. Lee
Assistant Examiner—Fiona T. Powers

[57] ABSTRACT

Compounds of the general formula $$R-N=NX \qquad (I)$$

or N-oxides thereof, where R represents on amidophenyl group, and X represents a cyano group, a group —COOH or a salt, ester or amino derivative thereof; are fungicidal.

6 Claims, No Drawings

BIOCIDAL AZOPHENYL COMPOUNDS

This invention relates to novel azophenyl compounds, to their use as biocidal, especially fungicidal, agents, to biocidal compositions containing such compounds, and to the preparation of such compounds.

Calvatic acid, (4-(cyano-N,N,O-azoxy)benzoic acid) and a limited number of analogous compounds, have been investigated in respect of their antibacterial and antifungal properties. Thus, in Trans. Mycol. Soc. Japan, 23, p. 225-234, 1984, calvatic acid and its methyl ester are described as having antibacterial and antifungal activity In Eur. J. Med. Chem-Chimica Therapeutica, January-February 1977-12 No. 1, p. 59-62, the preparation and screening of further analogues is described. The compounds made and tested were of the following formula:

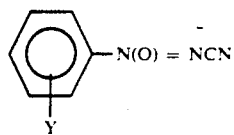

Y: 2-Cl; 3-Cl; 4-Cl;
2-Br; 3-Br; 4-Br;
2-NO$_2$; 3-NO$_2$; 4-NO$_2$;
2-OCH$_2$; 3-OCH$_2$; 4-OCH$_3$;
H;
p-N(CH$_3$)$_2$

Antibacterial and antifungal properties of 4-carboxyphenylazoxycyanide-dimethylsulphoxide are described in Acta Crystallogr., Sect. B, 1975, B31(8) p.2151-3.

The antibacterial properties of certain further compounds are described in Japanese Patent application (Kokai) J5 2071444 (Takara Shuzo KK). The compounds are said (in Chemical Abstract No. 87:167770) to be compounds of the formula given above, where X is 2-CH$_3$; 3-CH$_3$; 3-COOH; 3-Cl; 3,4-Cl$_2$; and 2,5-CH$_3$,Cl).

In the Journal of Antibiotics 6/1986, p.864-8, the preparation and bactericidal and fungicidal screening of 2-(cyano-N,N,O-azoxy)benzoic acid is described but it is said to show no relevant activity against the tested fungi, and show low activity against bacteria.

In U.S. Pat. Nos. 4558040 and 4550121 there is described the miticidal activity of (2-alkyl-3,4-dihydro2H-1-benzopyran-8-yl)diazenecarboxylic acid esters and (2-substituted-2,3-dihydrobenzo-furan-7-yl)diazenecarboxylic acid esters.

The present invention is based upon the discovery of certain novel compounds, and the subsequent discovery of their effectiveness in combating fungi, including plant pathogenic fungi.

According to a first aspect of the present invention there is provided a compound of the general formula $$R-N=N-X \qquad (I)$$

or an N-oxide thereof, where R represents a substituted phenyl group, at least one substituent thereof being an optionally substituted amido group; and X represents a cyano group, a group —COOH or a salt, ester or amido derivative thereof.

Unless otherwise specified in this specification, an alkyl group may be linear or branched and suitably contains up to 10, preferably up to 6, and most preferably up to 4, carbon atoms, preferred examples being methyl and ethyl.

Unless otherwise stated in this specification, when any groups are designated as being optionally substituted, the substituent groups which are optionally present may be any of those customarily employed in the development of pesticidal compounds, and/or the modification of such compounds to influence their structure/activity, persistence, penetration or other property. In relation to an alkyl group, specific examples of such substituents may include halogen, especially fluorine, chlorine or bromine atoms, and phenyl, alkoxy, hydroxy, cyano and (alkyl)amino groups. In relation to a phenyl moiety, optional substituents may include halogen atoms, for example fluorine, chlorine, bromine and iodine atoms, and nitro, cyano, alkoxy, hydroxy, (alkyl)amino, alkyl and haloalkyl (especially CF$_3$) groups.

An optionally substituted amido group is a group of general formula —CONR$^1$R$^2$ where each of R$^1$ and R$^2$ independently represents a hydrogen atom or an optionally substituted (preferably unsubstituted) alkyl group, or an optionally substituted phenyl group, preferably phenyl optionally substituted by one or more halogen atom(s), alkoxy, haloalkyl and/or alkyl group(s).

Preferably, each of R$^1$ and R$^2$ independently represents a hydrogen atom, a C$_{1-4}$ alkyl group, or an optionally halo-substituted phenyl group. Preferably, at least one of R$^1$ and R$^2$ represents a hydrogen atom, and the other of R$^1$ and R$^2$ represents a hydrogen atom, methyl group, phenyl group or halophenyl group.

Preferably, the phenyl group R carries only one substituent, preferably in the 2- or, most preferably, the 4- position.

Preferred compounds of general formula I are N-oxidised.

Preferably, X represents a cyano group, a group —COOH or a group —COOZ where Z represents a C$_{1-4}$ alkyl, alkenyl or alkynyl group, for example methyl, ethyl, allyl or propargyl. Most preferably, X represents a a cyano group.

It should be noted that compounds of the general formula I may exist as cis or trans isomers, and that the scope of the present invention covers any such isomers, isolated or together.

It should also be noted that N-oxidised compounds of general formula I could be in any of the following isoelectronic forms:

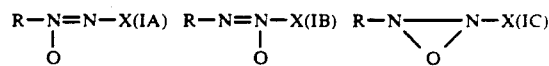

It is believed, on the basis of NMR analysis, that form IA is the preferred/dominant form, rather than form IB or IC, but it should be noted that the scope of the present invention covers any such forms.

In accordance with a second aspect of the present invention there is provided a method of combating a fungus at a locus, which comprises treating the locus with a compound of the general formula I, as defined in any of the preceding passages. In the method of the invention the locus may be an agricultural or horticultural locus, for example plants subject to attack, seeds of such plants or the medium in which such plants are growing or are to be grown. Compounds of the present invention have been shown to exhibit activity against a range of important fungi including vine downy mildew, vine grey mould, wheat leafspot, barley powdery mildew, tomato early blight, wheat eyespot, seedling wheat blight and wheat brown rust. Particularly consistent and high activity has been observed against vine downy mildew. A locus as described above may suitably be treated with a compound I at an application rate in the range of 0.05–4 Kg.ha, preferably 0.1–1 Kg/ha.

The invention further provides the use as a fungicide of a compound of the general formula I as defined in any of the above statements.

Compounds in accordance with general formula I have shown nematicidal activity and so a further aspect of the present invention provides the nematicidal use of compounds of general formula I.

Further in accordance with the invention there is provided a fungicidal composition which comprises a carrier and, as active ingredient, a compound of general formula I, as defined in any of the statements above.

A carrier in a composition according to the invention is any material with which the give active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating biocidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen, waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10% w of active ingredient. Granules are usually prepared to have a size between 10 and 100 BS mesh (1.676–0.152 mm), and may be manufactured by agglomeration or impregnation techniques. Generally, granules will contain 0.5–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick "mayonnaise"—like consistency.

The composition of the invention may also contain other ingredients, for example other compounds possessing herbicidal, insecticidal or fungicidal properties.

In accordance with a further aspect of the present invention there is provided a process for the preparation of compound of general formula I, as defined in any of the statements above, which comprises reacting a compound of the general formula R—N=O (II) with cyanamide, to form an N-oxide compound of general formula I wherein X represents a cyano group; and optionally derivatising that compound to produce a further novel compound of formula I.

Suitably the reaction takes place in the presence of an organic solvent, preferably a halogenated hydrocarbon, for example chloroform, and in the presence of iodobenzene diacetate. The reaction is preferably effected at a temperature in the range $-20°$ C. to $50°$ C., conveniently at ambient temperature.

Derivatisation of the compound of formula I may, for example, be effected by standard hydrolysis, in the presence of a strong acid or a strong base, to convert the cyano group to a carboxy group, or, stopping the reaction at an intermediate stage, an amido group.

Esters may be prepared by standard esterification of the resultant carboxylic acid or by acid alcoholysis of the cyano compound to form the acid salt of the imidate ester, which is reacted with water, suitably at ambient temperature, to yield the ester. Alternatively, esters may be prepared by the following general route, described in greater detail in U.S. Pat. Nos. 4558040 and 4550121:

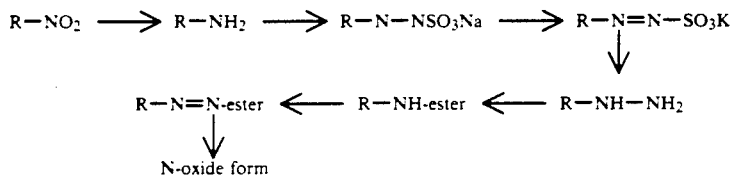

The latter two compounds may be converted to other compounds of formula I, for example amides, acids and nitriles, by standard methods.

A compound of formula II may be prepared as follows:

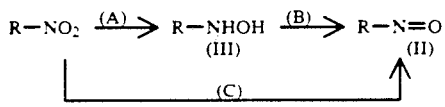

Reaction A may, for example, be effected by reaction of the nitro compound with hydrazine hydrate, in the presence of a hydrogen transfer catalyst, for example rhodium on carbon, suitably in the presence of an inert polar organic solvent, for example tetrahydrofuran, preferably at a temperature in the range $-20°$ C. to $50°$ C., conveniently at ambient temperature; or be effected using water, stannous chloride as reducing agent, an inert, polar organic solvent, for example tetrahydrofuran, under an inert atmosphere, for example nitrogen, in the presence of sodium acetate, suitably at ambient temperature.

Reaction B may suitably be effected by treatment of the hydroxylamine derivative with an oxidising agent, for example an $Fe^{3+}$ compound, suitably ferric chloride. The reaction may be effected in a mixed water/polar organic solvent, for example water/methanol, preferably with cooling.

Reaction C may be effected by irradiating the nitro compound, which is preferably dissolved in an inert organic solvent, for example benzene. The irradiation may be effected using a medium pressure mercury lamp.

The nitro, hydroxylamine and nitroso compounds are known or else may be prepared from known compounds by standard methods. Any such compounds which are novel constitute further aspects of the invention, together with methods for their preparation.

Novel unoxidised compounds of formula I may be made by analogous method to that described in U.S. Pat. No. 2910463 and Med. Chem- Chim Ther., 1982-17, No. 5,p. 482-4, wherein diazotization of an amine compound is carried out, and the resulting diazotised compound is cyanated, in the following manner.

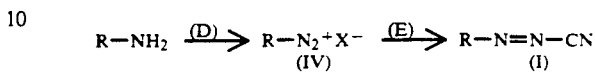

where $X^-$ is an anion derived from a mineral acid. Optionally, a resultant compound I may be derivatised, for example oxidised under standard conditions to yield an N-oxide compound of general formula I.

A typical oxidation method uses a "peroxy" compound, for example hydrogen peroxide, or a peroxycarboxylic acid in a suitable inert organic solvent, for example a halogenated hydrocarbon, such as dichloromethane, at a temperature in the range, suitably, $-20°$ to $60°$ C. Suitable "peroxy" acids include peroxytrifluoroacetic acid and metachloroperbenzoic acid.

For reaction D, standard diazotisation conditions are employed, for example a low temperature, suitably $-10°$ C. to $20°$ C., and sodium nitrite in an aqueous mineral acid.

For reaction E, cyanation is suitably effected by treating the compound of general formula IV with an alkali metal cyanide, for example sodium cyanide, suitably at a low temperature, for example $-20°$ C. to $+20°$ C., removing the aqueous layer, adding a halogenated hydrocarbon, for example carbon tetrachloride, and heating the organic layer, suitably at a temperature in the range $40°-100°$ C., preferably under reflux.

Steps D and E and/or the compounds of general formula IV may be new and if so constitute further aspects of the invention.

Other methods suitable for preparing compounds, of formula I, and further descriptions of the methods described herein, may be found in The Journal of Antibiotics, January 1975, p.87-90 and June 1986, p.864-868; in Eur.J.Med.Chem.-Chim.Ther.,1982,17, No. 5, p.482-484, and 1980, 15, No. 5, p.475-478, and 1977, 12, No. 1, p.59-62; in J.Chem.Soc., Chem. Commun., 1984, p.323-324; in Chem.Ind (Milan), 1977, 59(5), p. 385; in Gazetta Chimica Italiana, 106, 1976, p.1107-1110; in Tetrahedron Letters, No. 38, 1974, p. 3431-3432; and in U.S. Pat. Nos. 4558040 and 4550121.

The invention will now be further illustrated by the following examples.

EXAMPLE 1

Preparation of
[4-(N-phenylamido)phenyl]-ONN-azoxycyanide (R=4-(N-phenylamido)phenyl; X=cyano; N-oxide)

(4-N-phenylamido)nitrobenzene (10 g) was dissolved in tetrahydrofuran. Rhodium on carbon catalyst (0.2 g) was added and the reaction mixture was treated with hydrazine hydrate (2.4 mls), dropwise at ambient temperature. The reaction mixture was stirred for two hours at ambient temperature, then filtered though a HYFLO (Trade Mark) filter. The solvent was removed by evaporation. The resulting compound 4-(N-phenylamido)hydroxylaminobenzene (9.0 g) was added, crude, to methanol (30 ml), and the resulting solution was added to a solution of ferric chloride (22 g) in methanol/water (100/200 ml), at 20° C. The resultant compound, 4-(N-phenylamido)nitrosobenzene (7.2 g) was a yellow solid. 4.2 g of the product was added to dimethylformamide (100 ml) at 0° C., cyanamide (1.3 g) was added, and the reaction mixture was treated dropwise with iodobenzenediacetate (7.2 g) in chloroform (100 ml). The reaction mixture was stirred overnight at ambient temperature. The resultant brown solid was washed with chloroform to yield a yellow solid (1.2 g), mp 220°-225° C. (decomp.).

Analysis of recrystallised sample: Calc. %: C 63.2 H 3.8 N 21.1. Found %: C 63.8 H 3.8 N 19.8.

EXAMPLE 2

Preparation of 4-amidophenyl-azocyanide p-Amidobenzamide (13.6 g), in water (25 ml) and concentrated hydrochloric acid (25 ml), was diazotised by addition of sodium nitrite (13.6 g) in a minimum quantity of water. Ethyl acetate was added and the reaction mixture cooled to about $-5°$ C. A solution of sodium cyanide (6.5 g) in a minimum quantity of water was added dropwise, and the reaction mixture stirred, for two hours at 0° C. The reaction mixture was then filtered to yield the title compound, as a red solid (10.3 g), mp 188°-190° C. IR spectroscopy showed —CN at 2200 cm$^{-1}$. The organic layer was dried and the solvent removed to yield a red solid which was recrystallised from ethanol/water, and analysed. IR showed an identical compound to the initial product of filtration.

Analysis: Calc. %: C 55.2 H 3.5 N 32.2. Found %: C 55.2 H 3.7 N 32.1.

EXAMPLE 3

Preparation of 4-amidophenyl-ONN-azoxycyanide

The title compound of Example 2 (1.7 g) was added to trifluoracetic acid (10 ml) and 85% hydrogen peroxide/water (1.5 ml). The reaction mixture was heated for 5 hours at 45°-50° C., cooled, and poured into ice. The resultant yellow product was filtered off, washed with water and dried. The products was purified by flash chromatography on silica, using ethyl acetate as eluant, yielding the title compound (0.65 g), mp 235°-238° C.

Analysis: Calc. %: C 50.5 H 3.2 N 29.4. Found %: C 50.4 H 3.3 N 28.6.

Further examples were prepared according to techniques analogous to those described above, as follows:

EXAMPLE 4

Preparation of 2-amidophenyl-ONN-azoxycyanide mp 154° C. Analysis: Calc. %: C 51.1 H 2.0 N 28.0. Found %: C 50.6 H 3.2 N 29.5.

EXAMPLE 5

Preparation of
[2-(N-phenylamido)phenyl]-ONN-azoxycyanide mp 200° C. Analysis: Calc. %: C 62.4 H 3.8 N 20.6. Found %: C 63.2 H 3.8 N 21.1.

EXAMPLE 6

Preparation of
4-[(N-phenylamido)phenyl]-azoxycyanide mp 187°-188° C. (decomp.) Analysis: Calc. %: C 67.2 H 4.0 N 22.4. Found %: C 66.4 H 4.5 N 20.6.

EXAMPLE 7

Preparation of
[4-(N-methylamido)phenyl]-ONN-azoxycyanide mp 242°-243° C. (decomp.). Analysis: Calc %: C 52.9 H 4.0 N 27.4. Found %: C 52.1 H 4.3 N 24.9.

EXAMPLE 8

Preparation of
[4-{N-(2-chlorophenyl)amido}phenyl]-ONN-azoxycyanide mp 185°-186° C. (decomp.). Analysis: Calc. %: C 55.9 H3.0 N 18.6. Found %: C 55.0 H 3.4 N 17.8.

EXAMPLE B1

The fungicidal activity of compounds of the invention was investigated by means of the following tests.

(a) Direct protectant activity against vine downy mildew (Plasmopara viticola; Pvp)

The test is a direct protectant one, using a foliar spray. The lower surfaces of leaves of whole vine plants (cv Cabernet Sauvignon) are sprayed with a solution of active material in 1:1v/v water/acetone containing 0.04% w "Triton X-155" (trade mark) (octylphenol polyoxyethylene surfactant), at a dosage of 1 kilogram of active material per hectare using a track sprayer which delivers 620 liters/ha, and after a subsequent 24 hours under normal glasshouse conditions the lower surfaces of the leaves are inoculated by spraying with an aqueous solution containing $10^4$ zoosporangia/ml. The inoculated plants are kept for 24 hours in a high humidity compartment, 5 days under normal glasshouse conditions and then returned for a further 24 hours to high humidity. Assessment is based on the percentage of leaf area covered by sporulation compared with that on control leaves.

(b) Direct protectant activity against vine grey mould (Botrytis cinerea; Bcp)

The test is a direct protectant one using a foliar spray and is effected as described under (a), with the difference that the leaves are inoculated by spraying with an aqueous solution containing $10^5$ conidia/ml.

(c) Activity against wheat eyespot
(Pseudocereosporella herpotrichoides; Ph)

The test is an in vitro one. Samples are prepared wherein 0.7 mls solution containing 2 mg active material dissolved in acetone is evenly dispersed in 20 ml molten half-strength potato dextrose agar (formed by dissolving 2 g potato extract, 10 g dextrose and 7.5 g agar in 1 liter of water and sterilising for 15 minutes at 121° C.) and the resulting 20 ml portions are allowed to set in 9 cm petri dishes. The concentration of active material in the resulting samples is 100 ppm. Upon setting, two plugs of 5 mm diameter taken from the advancing edge of a stock plate of a 3 to 4 week old culture of *P.herpotrichoides* on full strength potato dextrose agar, incubated at 20°-22° C. in darkness, are placed, equally spaced on the surface of each sample, mycelial side uppermost. The samples are incubated for 11 days at 20°-22° C. in darkness before assessment. Diametric growth is measured with the width of the plug subtracted and results compared with growth on a sample wherein 0.7 ml acetone containing no active material is dispersed in 20 ml half-strength potato agar.

(d) Activity against seedling wheat blight (Fusarium culmorium: Fs)

The test is an anti-sporulant one using a soil drench. Surface sterilised wheat seeds (var Waggoner) are inoculated by soaking in an aqueous suspension containing $7 \times 10^5$ spores/ml (60 mg seed per 80 ml suspension) at 22° C. for 6 hours.. The seeds are then sown in pots (5 per pot) in sand at a depth of 1 cm. 1 day after inoculation and planting the active material is applied at a rate of 10 kg/ha by pouring on a soil drench (concentration 0.36 g/l active material in 12% v/v acetone/water) evenly over the sand. The pots are then transferred to glasshouse, kept at 25° C. and watered sparingly. 21 days after inoculation the resulting seedlings are removed from the pots and their roots are gently washed. Visual assessment is made based on lesion development on stem base and upper roots in comparison with control seedlings.

(e) Activity against wheat leafspot (Leptosphaeria nodorum; Ln)

The test is a direct antisporulant one, using a foliar spray. Leaves of wheat plants (cv Mardler), at the single leaf stage, are inoculated by spraying with an aqueous suspension containing $8 \times 10^5$ spores/ml. The inoculated plants are kept for 24 hours in a high humidity compartment prior to treatment. The plants are sprayed at a dosage of 1 kg. of active material per hectare using a track sprayer as described under (a). After drying, the plants are kept for 5 days under normal glasshouse conditions, followed by assessment. Assessment is based on the percentage of leaf area covered by sporulation compared with that on leaves of control plants.

(f) Activity against barley powdery mildew (Erysiphe graminis f.sp. hordei; Eg)

The test is a direct antisporulant one, using a foliar spray. Leaves of barley seedlings, cultivar Golden Promise, are inoculated by dusting with mildew conidia one day prior to treatment with the test compound. The inoculated plants are kept overnight at glasshouse ambient temperature and humidity prior to treatment. The plants are sprayed at a dosage of 1 kg. of active material per hectare using a track sprayer as described under (a). After drying, plants are returned to a compartment at ambient temperature and humidity for up to 7 days, followed by assessment. Assessment is based on the percentage of leaf area covered by sporulation compared with that on leaves of control plants.

(g) Activity against tomato early blight (Alternaria Solani;As)

The test is a direct protectant one using a foliar spray. The upper surfaces of leaves of young tomato plants are sprayed with a solution of active material as described in (a) above. After 24 hours under normal glasshouse conditions, the upper surfaces of the leaves are inoculated by spraying with an aqueous suspension containing $10^4$ spores/ml. The inoculated plants are kept for 72 hours in a high humidity compartment and are then removed to lower humidity (50-70% relative humidity). Assessment is made 8 days after inoculation.

(h) Activity against wheat brown rust (Puccinia Recondita; Pr)

The test is a direct protectant one using a foliar spray. Wheat seedlings (cv Brigand) are grown to the 1-1.5 leaf stage. The plants are then sprayed with the test compound at a dosage of 1 Kg/ha using a track sprayer as described under (a). Test compounds are applied as solutions or suspensions in a mixture of acetone and water (50:50 v/v) containing 0.04% surfactant ("TWEEN 20"-Trade Mark).

18-24 hours after treatment, the seedlings are inoculated by spraying the plants from all sides with an aqueous spore suspension containing about $10^5$ spores/ml For 18 hours after inoculation, the plants are kept in high humidity conditions at a temperature of 20°-22° C. Thereafter, the plants are kept in ambient glasshouse conditions, that is, in moderate relative humidity and at ambient temperature of 20° C.

The disease is assessed 10 days after inoculation on the basis of the percentage of the plant covered by sporulating pustules compared with that on the control plants.

The results of the above tests are given in Table 1 below.

TABLE 1

| Ex. No. | Pvp | Bcp | Ph | Fs | Ln | Eg | As | Pr |
|---|---|---|---|---|---|---|---|---|
| 1 | 2 | 2 | | | | | 2 | 1 |
| 2 | 2 | 2 | | | | | | |
| 3 | 2 | 2 | 2 | 2 | 1 | | 2 | |
| 4 | 2 | | 1 | 1 | 1 | 1 | | 1 |
| 5 | 2 | 1 | 2 | 2 | | | 1 | 1 |

The extent of disease control in all the above tests is expressed as a rating compared with either an untreated control or a diluent-sprayed-control, according to the criteria:

0 = less than 50% disease control,
1 = about 50-80% disease control, and
2 = greater than 80% disease control.

The fungicidal activity of the compounds was investigated further, in secondary screening, against fungi against which promising results from primary screening had been obtained. These confirmed that certain compounds have particularly high activity against certain fungi. Examples 1 and 3 were found to have high activity against As and Pvt (Plasmopara viticola as determined by a translaminar protectant test, in which the upper surfaces of the leaves of whole vine plants are sprayed with a solution of the compound, and the lower leaves are then inoculated with the appropriate Zoosporangia); and Example 5, against Pvt.

Compounds described above also showed nematicidal activity.

We claim:

1. A compound of the formula:

$$R-N=N-X \quad (I)$$

or an N-oxide thereof, wherein R represents a phenyl group which is substituted by a group of the formula —CONR$^1$R$^2$ wherein each of R$^1$ and R$^2$ independently represents a hydrogen atom or an alkyl group, optionally substituted by a halogen atom or a phenyl, alkoxy, hydroxy, cyano or (alkyl) amino group, or a phenyl group optionally substituted by a halogen atom or a nitro, cyano, alkoxy, hydroxy, (alkyl) amino, alkyl or haloalkyl group, and X represents a cyano group, a —COOH group or a salt, ester or amido derivative thereof.

2. A compound of claim 1, wherein X represents a cyano group.

3. A compound of claim 2, wherein R represents a phenyl group which is substituted by a group of the formula —CONHR$^1$ wherein R$^1$ represents a hydrogen atom, an alkyl group, a phenyl group, or a halophenyl group.

4. A fungicidal composition which comprises a carrier and as an active ingredient an effective amount of a compound of formula (I) as claimed in claim 1.

5. A method of combating a fungus at a locus, which method comprises treating said locus with an effective amount of a compound of formula (I) as claimed in claim 1.

6. A method of combating a fungus at a locus, which method comprises treating said locus with an effective amount of a composition as claimed in claim 4.

* * * * *